United States Patent
Neuner

(10) Patent No.: US 8,361,445 B2
(45) Date of Patent: Jan. 29, 2013

(54) FORMULATIONS FOR TREATING AND/OR PREVENTING BLACK-LINE STAINS

(76) Inventor: Ketty Neuner, Raanana (IL)

( * ) Notice: Subject to any disclaimer, the term of this patent is extended or adjusted under 35 U.S.C. 154(b) by 101 days.

(21) Appl. No.: 12/985,112

(22) Filed: Jan. 5, 2011

(65) Prior Publication Data

US 2011/0256073 A1 Oct. 20, 2011

Related U.S. Application Data

(60) Provisional application No. 61/294,586, filed on Jan. 13, 2010.

(51) Int. Cl.
*A61K 8/96* (2006.01)
*A61K 8/21* (2006.01)
*A61K 8/00* (2006.01)

(52) U.S. Cl. .................. 424/50; 424/52; 424/53; 424/54

(58) Field of Classification Search .................... 424/50, 424/52, 53, 54
See application file for complete search history.

(56) References Cited

U.S. PATENT DOCUMENTS 7,758,888 B2 * 7/2010 Lapidot et al. ................ 424/489

* cited by examiner

*Primary Examiner* — Raymond Henley, III
(74) *Attorney, Agent, or Firm* — Pearl Cohen Zedek Latzer, LLP

(57) ABSTRACT

The present invention is directed to the use of antibiotics for preparing topical oral antibiotic formulations for treating and/or preventing black-line stains. This invention is further directed to a method of treating and/or preventing black-line stains comprising administration of a topical oral antibiotic formulation. The invention is additionally directed to a topical oral antibiotic formulation for use in treating and/or preventing black-line stains.

24 Claims, No Drawings

FORMULATIONS FOR TREATING AND/OR PREVENTING BLACK-LINE STAINS

This application claims priority to provisional application No. 61/294,586, filed Jan. 13, 2010.

FIELD OF THE INVENTION

The invention is directed to the use of antibiotics for preparing topical oral antibiotic formulations for treating and/or preventing black-line stains. This invention is further directed to a method of treating and/or preventing black-line stains comprising administration of a topical oral antibiotic formulation. The invention is additionally directed to a topical oral antibiotic formulation for use in treating and/or preventing black-line stains.

BACKGROUND OF THE INVENTION

Black-line stains on teeth is a well known phenomenon, which relates to black stains appearing on teeth, generally more prevalent near the gums and on the back teeth, though can appear on any teeth and may be distributed on the entire tooth, not only near the gums.

Though the cause for the black-line stains is not fully known, it is thought to be partially caused by dental plaque in the same manner as other topical stains on teeth are caused. Although, dental plaque is caused by bacteria, the type of bacteria that causes black-stains is probably different than that which causes other stains. It is thought that lactobacillus, which is a genus of Gram-positive, facultative anaerobic or microaerophilic bacteria, is the cause of the plaque on teeth that results in black line stain. Generally, black-line stains are more prevalent in children, though can appear in adults as well.

Gingival scrapings from the teeth of patients with black-line stains have been shown to contain high phosphate content as well as high calcium content. Further testing has shown an insoluble iron compound in the black-line stain. It is thought that the lactobacillus, or possibly other bacteria, and the insoluble iron compound may cause of black-line stain. Further, it is thought that the insoluble iron compound is formed due to the interaction of hydrogen sulfide produced by the bacteria and the iron in the saliva or gingival fluids.

Although the black-line stains are medically harmless, they are not esthetic. Further, the removal of black-line stains is difficult, and may be performed by scaling and polishing by a dentist or a dental hygienist. Additionally, once removed, the black-stains tend to recur, even if the patient takes all necessary oral hygiene measures.

Currently, there are no known formulations, mouthwashes, toothpastes, toothbrushes and the like for treating the black-line staining. Thus, there is a need in the art for such treatments.

SUMMARY OF THE INVENTION

In an embodiment of the invention, there is provided a method of treating, preventing or treating and preventing black-line stains comprising the step of contacting of a topical oral antibiotic formulation with teeth.

In another embodiment, the invention relates to the use of at least one antibiotic for the preparation of a topical oral formulation for the treatment, prevention or treatment and prevention of black-line stains on the teeth.

A topical oral formulation for use in treating, preventing or treating and preventing black-line stains, comprising at least one antibiotic.

In an embodiment of the invention, there is provided a kit, including the topical formulation or any other dosage form described herein (for example stickers) together with a label, which comprises directions as to the dosage regimen and to the method of applying the formulation or the dosage form onto the teeth.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention relates to the use of an antibiotic solution for preparing topical oral formulations for the treatment and/or prevention of black-line stains.

This invention further relates to a method of treating and/or preventing black-line stains comprising the step of contacting of a topical oral formulation containing at least one antibiotic medicament to the teeth.

This invention additionally relates to a topical oral antibiotic formulation for use in treating and/or preventing black-line stains. The topical oral is applied the teeth. The topical antibiotics is applied as a rinse.

According to this invention, the black-line stain may be mechanically removed from the teeth prior to the application of the topical oral antibiotic formulation to the teeth.

According to this invention the antibiotic may be any appropriate antibiotic, such as tetracycline, chlortetracycline, clomocycline, demeclocycline, doxycycline, lymecycline, meclocyline, metacycline, minocycline, oxytetracycline, penimepicycline, periostat, rolitetracycline, penicillin, cephalosporin, emoxycillin, etc. According to an embodiment of this invention, the antibiotic is tetracycline.

As used herein, the term "topical oral antibiotic formulation" is a formulation comprising an antibiotic drug that is applied to the interior of the mouth, though is not swallowed. The formulation according to this invention may therefore be any appropriate type of topical oral formulation, including a solution, suspension, dispersion, mouthwash, toothpaste, oral gel, paste, ointment, chewable tablets, dissolvable tablets, capsules, stickers, small towels including the same and the like.

One embodiment of the invention is the use of at least one antibiotic to prepare a topical oral antibiotic formulation e.g., a mouthwash, solution, suspension or dispersion, for the treatment and/or prevention of black-line stains, comprising dissolving the antibiotic in any appropriate fluid, e.g., water, to prepare the formulation; applying the formulation to the interior of the mouth for an appropriate period of time; and removing the formulation from the mouth, with or without additional washing of the mouth.

Another embodiment of the invention is a method of treating and/or preventing black-line stains with a topical oral antibiotic solution, suspension or dispersion formulation, e.g., a mouthwash, comprising dissolving the antibiotic in any appropriate fluid, e.g., water, to prepare the formulation; applying the formulation to the interior of the mouth for an appropriate period of time; and removing the formulation from the mouth, with or without additional washing of the mouth.

Another embodiment of the invention is a topical oral antibiotic solution, suspension or dispersion formulation, e.g., a mouthwash, for use in treating black line stains, comprising dissolving the antibiotic in any appropriate fluid, e.g., water, to prepare the formulation; applying the formulation to the interior of the mouth for an appropriate period of time; and removing the formulation from the mouth, with or without additional washing of the mouth.

In an embodiment of the invention the concentration of the antibiotic in the formulation is between about 1000. 500 or 250 mg/100 ml.

According to one embodiment of the invention, the formulation remains in the mouth for approximately 5, 10, 15, 20, 25, 30, 35, 40, 45, 50, 55, 60, 80, 100, 120, 180 or more seconds. In some embodiment, the formulation remains for overnight treatment, for a day or more.

A further embodiment of the invention is the use of at least one antibiotic to prepare a paste or a gel for treating and/or preventing black-line stains, comprising the application of the paste/gel to the teeth by any appropriate means, e.g., a toothbrush. The paste/gel is then left on the teeth for an appropriate period of time, e.g., approximately 5, 10, 15, 20, 25, 30, 35, 40, 45, 50, 55, 60, 80, 100, 120, 180 or more seconds, and then removed from the mouth by washing with any appropriate fluid, which may be water. The treatment time will be calculated according to the dosing and vice versa.

Another embodiment of the invention is a method of treating and/or preventing black-line stains comprising the application of a paste or gel to the teeth by any appropriate means, e.g., a toothbrush. The paste/gel is then left on the teeth for an appropriate period of time, e.g., approximately 5, 10, 15, 20, 25, 30, 35, 40, 45, 50, 55, 60, 80, 100, 120, 180 or more seconds, and then removed from the mouth by washing with any appropriate fluid, which may be water. In some embodiment, the formulation remains for overnight treatment, for a day or more.

A further embodiment of the invention is a paste or gel formulation for use in treating and/or preventing black-line stains, comprising the application of the paste/gel to the teeth by any appropriate means, e.g., a toothbrush. The paste/gel is then left on the teeth for an appropriate period of time, e.g., approximately 5, 10, 15, 20, 25, 30, 35, 40, 45, 50, 55, 60, 80, 100, 120, 180 or more seconds, and then removed from the mouth by washing with any appropriate fluid, which may be water.

Another embodiment of the invention is the use of at least one antibiotic to prepare a chewable tablet for treating and/or preventing black-line stains, wherein the tablet is chewed by the patient. The particles of the chewable tablet are left on the teeth for an appropriate period of time, e.g., approximately 5, 10, 15, 20, 25, 30, 35, 40, 45, 50, 55, 60, 80, 100, 120, 180 or more seconds, and then removed from the mouth by washing with any appropriate fluid, which may be water.

Another embodiment of the invention is a method of treating and/or preventing black-line stains comprising the administration of a chewable tablet comprising at least one antibiotic, wherein the tablet is chewed by the patient. The particles of the chewable tablet are left on the teeth for an appropriate period of time, e.g., approximately 5, 10, 15, 20, 25, 30, 35, 40, 45, 50, 55, 60, 80, 100, 120, 180 or more seconds, and then removed from the mouth by washing with any appropriate fluid, which may be water.

Another embodiment of the invention is a chewable tablet comprising at least one antibiotic for use in treating and/or preventing black-line stains, wherein the tablet is chewed by the patient. The particles of the chewable tablet are left on the teeth for an appropriate period of time, e.g., approximately 5, 10, 15, 20, 25, 30, 35, 40, 45, 50, 55, 60, 80, 100, 120, 180 or more seconds, and then removed from the mouth by washing with any appropriate fluid, which may be water.

A further embodiment of the invention is the use of at least one antibiotic to prepare a dissolvable tablet for treating and/or preventing black-line stains, wherein the dissolvable tablet is dissolved in any appropriate fluid, which may be water, thereby forming a solution/suspension/dispersion. The solution/suspension/dispersion is then applied to the interior of the mouth for an appropriate period of time, e.g., approximately 5, 10, 15, 20, 25, 30, 35, 40, 45, 50, 55, 60, 80, 100, 120, 180 or more seconds, and then removed from the mouth, with or without additional washing of the mouth.

An additional embodiment of the invention is a method of treating and/or preventing black-line stains comprising the administration of a dissolvable tablet comprising at least one antibiotic, wherein the dissolvable tablet is dissolved in any appropriate fluid, which may be water, thereby forming a solution/suspension/dispersion. The solution/suspension/dispersion is then applied to the interior of the mouth for an appropriate period of time, e.g., approximately 5, 10, 15, 20, 25, 30, 35, 40, 45, 50, 55, 60, 80, 100, 120, 180 or more seconds, and then removed from the mouth, with or without additional washing of the mouth.

Another embodiment of the invention is a dissolvable tablet comprising at least one antibiotic for use in treating and/or preventing black-line stains, wherein the dissolvable tablet is dissolved in any appropriate fluid, which may be water, thereby forming a solution/suspension/dispersion. The solution/suspension/dispersion is then applied to the interior of the mouth for an appropriate period of time, e.g., approximately 5, 10, 15, 20, 25, 30, 35, 40, 45, 50, 55, 60, 80, 100, 120, 180 or more seconds, and then removed from the mouth, with or without additional washing of the mouth.

Another embodiment of the invention is the use of at least one antibiotic to prepare a capsule for the treatment and/or prevention of black-line stains, wherein the capsule is dissolved in, or emptied into, any appropriate fluid, which may be water, thereby forming a solution/suspension/dispersion. The solution/suspension/dispersion is then applied to the interior of the mouth for an appropriate period of time, e.g., approximately 5, 10, 15, 20, 25, 30, 35, 40, 45, 50, 55, 60, 80, 100, 120, 180 or more seconds, and then removed from the mouth, with or without additional washing of the mouth.

Another embodiment of the invention is a method of treating and/or preventing black-line stains comprising administering a capsule comprising at least one antibiotic, wherein the capsule is dissolved in, or emptied into, any appropriate fluid, which may be water, thereby forming a solution/suspension/dispersion. The solution/suspension/dispersion is then applied to the interior of the mouth for an appropriate period of time, e.g., approximately 5, 10, 15, 20, 25, 30, 35, 40, 45, 50, 55, 60, 80, 100, 120, 180 or more seconds, and then removed from the mouth, with or without additional washing of the mouth.

Another embodiment of the invention is a capsule comprising at least one antibiotic for use in the treatment and/or prevention of black-line stains, wherein the capsule is dissolved in, or emptied into, any appropriate fluid, which may be water, thereby forming a solution/suspension/dispersion. The solution/suspension/dispersion is then applied to the interior of the mouth for an appropriate period of time, e.g., approximately 5, 10, 15, 20, 25, 30, 35, 40, 45, 50, 55, 60, 80, 100, 120, 180 or more seconds, and then removed from the mouth, with or without additional washing of the mouth.

In an embodiment of the invention comprises the application of the formulation any appropriate number of times a day, including, once, twice, three or less than ten times a day or an overnight treatment.

Another embodiment of the invention comprises the application of the formulation any appropriate number of times a week, including, every other day, twice a week, once a week, etc.

A further embodiment of the invention comprises the application of the formulation for any appropriate length of time, including three days, a week, two weeks, three weeks, a month, two months, six months or a year.

An additional embodiment of the invention comprises the application of the formulation twice a day for a week.

According to the invention, the formulation may include at least one additional component, such as colorant, flavoring, thymol, eucalyptol, hexetidine, methyl salicylate, menthol, chlorhexidine gluconate, benzalkonium chloride, cetylpyridinium chloride, methylparaben, hydrogen peroxide, domiphen bromide, fluoride, enzymes, calcium, alcohol, preservatives, sodium monofluorophosphate ($Na_2PO_3F$), organic amine fluoride, sodium lauryl sulphate, vitamins and herbs.

In an embodiment of the invention, there is provided a kit, including the formulation or any other dosage form described herein (for example stickers) together with a label, which comprises explanations to the dosage regimen and to the method of applying the formulation or the dosage form onto the teeth.

Various aspects of the invention are described in greater detail in the following Example, which represent embodiments of this invention, and are by no means to be interpreted as limiting the scope of this invention.

EXAMPLE

Two patients, who suffered from recurring black-line and whose teeth were cleaned by a dental hygienist, were treated twice a day for a week with a solution prepared by dissolving 250 mg capsules of tetracycline in 100 ml of water.

Neither one of the patients experienced the usual recurrence of the black-line (the first patient was monitored for two years and the second for half a year). Additionally, neither one of the patients experienced any adverse effects.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of treating, black-line stains comprising the step of applying a topical oral antibiotic formulation to teeth.

2. The method according to claim 1, wherein the black-line stains are removed from the teeth prior to the application of the topical oral antibiotic formulation to the teeth.

3. The method according to claim 1 wherein the antibiotic is selected from the group consisting of tetracycline, chlortetracycline, clomocycline, demeclocycline, doxycycline, lymecycline, meclocyline, metacycline, minocycline, oxytetracycline, penimepicycline, periostat, rolitetracycline, penicillin, cephalosporin and emoxycillin.

4. The method according to claim 1, wherein the antibiotic is tetracycline.

5. The method according to claim 1, wherein the formulation is a solution, ointment, paste, suspension, dispersion, mouthwash, toothpaste, oral gel, chewable tablet, dissolvable tablet, or capsule or is applied to a sticker or a small towel.

6. The method according to claim 1, wherein the formulation is applied to the teeth with a toothbrush.

7. The method according to claim 1, comprising the application of the formulation once, twice or three times a day or once, twice or three times a week.

8. The method according to claim 1, wherein the formulation further comprises at least one additional component selected from the group consisting of colorant, flavoring, thymol, eucalyptol, hexetidine, methyl salicylate, menthol, benzalkonium chloride, cetylpyridinium chloride, methylparaben, hydrogen peroxide, domiphen bromide, fluoride, enzymes, calcium, alcohol, preservatives, sodium monofluorophosphate ($Na_2PO_3F$), organic amine fluoride, sodium lauryl sulphate, vitamins and herbs.

9. A topical dental oral formulation comprising of at least one antibiotic, in an effective amount to treat, or treat and prevent the occurrence of black-line stain.

10. The formulation according to claim 9, wherein the black-line stains are removed from the teeth prior to the application of the topical oral antibiotic formulation to the teeth.

11. The formulation according to claim 9 wherein the antibiotic is selected from the group consisting of tetracycline, chlortetracycline, clomocycline, demeclocycline, doxycycline, lymecycline, meclocyline, metacycline, minocycline, oxytetracycline, penimepicycline, periostat, rolitetracycline, penicillin, cephalosporin and emoxycillin.

12. The formulation according to claim 9, wherein the antibiotic is tetracycline.

13. The formulation according to claim 9, wherein the formulation is a solution, ointment, paste, suspension, dispersion, mouthwash, toothpaste, oral gel, chewable tablet, dissolvable tablet, sticker, small towel or capsule.

14. The formulation according to claim 9, wherein the formulation further comprises at least one additional component selected from the group consisting of colorant, flavoring, thymol, eucalyptol, hexetidine, methyl salicylate, menthol, benzalkonium chloride, cetylpyridinium chloride, methylparaben, hydrogen peroxide, domiphen bromide, fluoride, enzymes, calcium, alcohol, preservatives, sodium monofluorophosphate ($Na_2PO_3F$), organic amine fluoride, sodium lauryl sulphate, vitamins and herbs.

15. A method of preventing the recurrence of black-line stains comprising the step of contacting of a topical oral antibiotic formulation with teeth.

16. The method according to claim 15, wherein the black-line stains are removed from the teeth prior to the application of the topical oral antibiotic formulation to the teeth.

17. The method according to claim 15, wherein the antibiotic is selected from tetracycline, chlortetracycline, clomocycline, demeclocycline, doxycycline, lymecycline, meclocyline, metacycline, minocycline, oxytetracycline, penimepicycline, periostat, rolitetracycline, penicillin, cephalosporin and emoxycillin.

18. The method according to claim 15, wherein the antibiotic is tetracycline.

19. The method according to claim 15, wherein the formulation is a solution, ointment, paste, suspension, dispersion, mouthwash, toothpaste, oral gel, chewable tablet, dissolvable tablet, or capsule or is applied to a sticker or a small towel.

20. The method according to claim 15, comprising the application of the formulation to the teeth with a toothbrush.

21. The method according to claim 15, comprising the application of the formulation once, twice or three times a day or once twice or three times a week.

22. The method according to claim 15, wherein the formulation further comprises at least one additional component selected from the group consisting of colorant, flavoring, thymol, eucalyptol, hexetidine, methyl salicylate, menthol, benzalkonium chloride, cetylpyridinium chloride, methylparaben, hydrogen peroxide, domiphen bromide, fluoride, enzymes, calcium, alcohol, preservatives, sodium monofluorophosphate (Na$_2$PO$_3$F), organic amine fluoride, sodium lauryl sulphate, vitamins and herbs.

23. A kit comprising a topical dental oral formulation comprising of at least one antibiotic and a label which comprises explanations to the dosage regimen and to the method of applying the formulation or the dosage form onto the teeth.

24. A topical dental oral formulation according to claim 9, wherein the formulation is prepared by dissolving the at least one antibiotic in a carrier.

\* \* \* \* \*